Jan. 29, 1957 W. E. LAMMERTS Plant Pat. 1,558
ROSE PLANT
Filed April 16, 1956
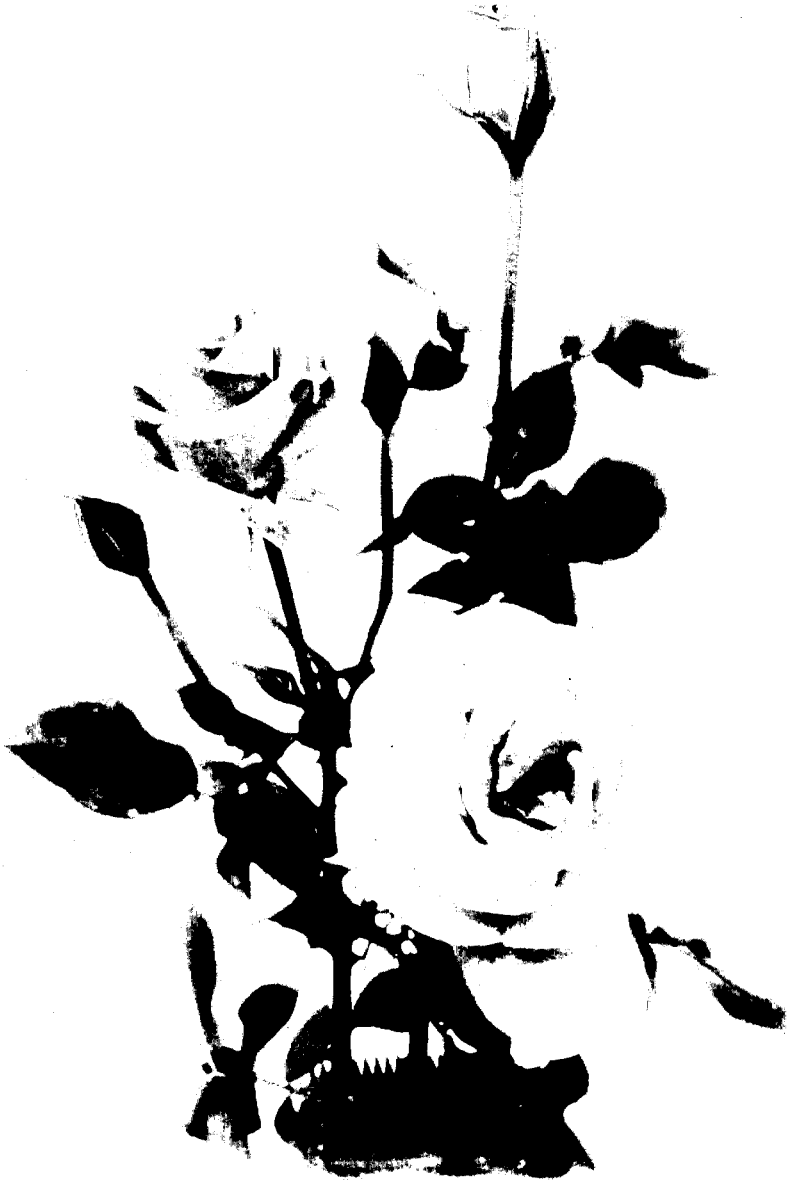
Inventor.
W. E. Lammerts
By: Robbins Cobb
Attorneys.

United States Patent Office

Plant Pat. 1,558
Patented Jan. 29, 1957

1,558

ROSE PLANT

Walter E. Lammerts, Livermore, Calif., assignor by mesne assignments, to Roseway Nurseries, Portland, Oreg., a partnership Application April 16, 1956, Serial No. 578,554

1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Grand Duchess Charlotte" (Plant Patent No. 774).

As the result of this cross, I have produced a new rose variety having foliage characteristics resembling those of the parent, "Grand Duchess Charlotte," but which otherwise is distinctly different from both parents, as well as from all other varieties of its class of which I am aware, as evidenced by the following characteristics:

(1) The vigorous, upright and tall habits of growth, with the height averaging several feet taller than the usual height of "Grand Duchess Charlotte" when grown under comparable coltoral conditions;

(2) The relatively long cutting stems;

(3) The long urn-shaped to long-pointed buds, somewhat resembling those of the variety "Eclipse" (Plant Patent No. 172); and (4) The vivid, velvety, glowing and unusually uniform Cherry to Orient Red general color tonality of the open flowers.

The foregoing characteristics, taken together, represent a unique and desirable combination which has never before been attained to my knowledge in a hybrid tea rose, and the resultant attractiveness of my new variety makes it especially desirable and valuable for garden decoration.

A sexual reproduction of the new variety by both grafting and budding, as performed by me at Livermore, California, shows that the foregoing characteristics and distinctions come true to form and are established and transmitted through succeeding propagations.

The accompanying drawing shows typical specimens of the vegetative growth and flowers of my new variety in different stages of development and as depicted in color.

The following is a detailed description of my new variety, with color terminology on accordance with the Horticultural Color Chart of the British Color Council, except where general color terms of ordinary dictionary significance are obvious:

Type: Hardy; tall; bush; outdoor; seedling; for garden decoration.

Class: Hybrid tea.

Breeding: Seedling.

*Seed parent.*—"Charlotte Armstrong."

*Pollen parent.*—"Grand Duchess Charlotte."

Propagation: Holds its distinguishing characteristics through succeeding propagations by both grafting and budding.

FLOWER

Locality where grown and observed: Livermore, California.

Flowers borne: Sometimes singly, and sometimes 2 or 3 to stem; on strong, long stems.

Quantity of bloom: Abundant, outdoors.

Continuity: Continuous.

Fragrance: Moderate. Nature—spicy.

Bud:

*Peduncle.*—Medium length; medium caliper; erect; stiff; almost smooth; with numerous reddish green, very small prickles and many glandtipped hairs. Color—Reddish Green.

*Before calyx breaks.*—Size—medium. Form—long; urn-shaped to long-pointed; without foliaceous appendages on the surface of the bud; with foliaceous parts extending beyond the tip of the bud equal to ¾ or more of its length. Color—Chrysanthemum Crimson, Plate 824/1.

*As calyx breaks.*—Color—Cardinal Red, Plate 822/1.

*As first petal opens.*—Size—Large. Form—very long; pointed. Color: Outside—Currant Red, Plate 821/2; Inside—from Cherry, Plate 722 near margin, to Orient Red, Plate 819 near center.

*Opening.*—Opens up well; opening is accelerated during hot weather.

Bloom:

*Size (when fully open).*—Large; from 4½ inches to 5½ inches.

*Petalage.*—From 18 to 22 petals; arranged regularly.

*Form.*—High-centered at first, but becoming flat; petals being at first tightly rolled inward, but later becoming loosely rolled outward at maturity.

Petals:

*Texture.*—Medium heavy; soft; with both inside and outside velvety.

*Shape.*—Outside—obovate, with apex having 2 notches. Intermediate—obovate-lanceolate, with short-pointed apex and occasionally 1 notch. Inside—Obovate-lanceolate, with apex having 1 notch usually of a very irregular shape.

This description of a newly opened flower was made from a rose grown outdoors in the month of September, at Livermore, California:

*Color.*—Outer petal: Outside surface—Current Red, Plate 821/2; inside surface—Rose Red, Plate 724 near margin, shading from Cherry, Plate 722 to Orient Red, Plate 819 near center. Intermediate petal: Outside surface—Current Red, Plate 821/2; inside surface—Rose Red, Plate 724 near margin, shading from Cherry, Plate 722 to Orient Red, Plate 819 near center. Inner petal: Outside surface—Current Red, Plate 821/2; inside surface—Rose Red, Plate 724 near margin, shading from Cherry, Plate 722 to Orient Red, Plate 819 near center.

This description was made from a rose that was open for 3 days outdoors in the month of September, at Livermore, California:

*Color.*—Outer petal: Outside surface—from Rose Bengal, Plate 25 to Solferino Purple, Plate 26; inside surface—from Tyrian Purple, Plate 727/1 to Rose Red, Plate 724/2. Inside petal: Outside surface—from Rose Bengal, Plate 25 to Solferino Purple, Plate 26; inside surface—from Tyrian Purple, Plate 727/1 to Rose Red, Plate 724/2.

*General color effect.*—Newly opened flower—from Cherry, Plate 722 to Orient Red, Plate 819, and remarkably uniform in color. 3-days open—Rose Red, Plate 724/2.

*Behavior.*—Drop off cleanly; fading to Rose Red, Plate 724; bud length and flower size decreases and opening of flowers accelerates with hot weather.

*Flower longevity.*—On bush in garden—3 days in September. Cut roses grown outdoors and kept at living-room temperatures—3 days in September.

REPRODUCTIVE ORGANS

Stamens: Many; arranged irregularly about pistils; mixed with petaloids.

Filaments: Variable, with a few only as long as pistils, but most from 2 to 3 times longer than pistils; most with anthers. Color—Mandarin Red, Plate 17, shading to Saturn Red, plate 13/1 near attachment to anthers.

Anthers: Medium size; open at various times. Color—Maize Yellow, Plate 607/1.

Pollen: Moderate. Color—Gold.

Pistils: Many.

Styles: Uneven (center ones short, but outer ones somewhat longer); thin; loosely columnar.

Stigma: Color—Yellow.

Ovaries: All enclosed in calyx tube.

Hips: Globular; with inconspicuous neck; smooth; walls thick and fleshy. Color—Yellow.

Sepals: Permanent; long; spear-shaped; recurved. Color—Lavender Green, Plate 000761/1.

Seeds: Few; medium size.

PLANT

Foliage:

*Leaves.*—Compound of 5 to 7 leaflets; large; moderately leathery.

*Leaflets.*—Shape—from long oval to ovoid, with apex acute to mucronate. Base—round. Margin—simply serrate.

*Color.*—Mature: Upper surface—Spinach Green, Plate 0960; under surface—near Lavender Green, Plate 000761. Young: Upper surface—Spinach Green, Plate 0960/2, tinged with Bronze; under surface—Lavender Green, Plate 000761/1, tinged with Bronze.

*Rachis (the supporting stem of the compound leaf).*—Medium caliper. Upper side—smooth; grooved. Under side—Sparsely prickly, with from 2 to 6 small prickles.

*Stipules.*—Medium length; medium width; with medium length points turning out at an angle of about 45°.

*Disease resistance.*—Moderately subject to mildew, as compared with other varieties grown under comparable cultural condition sat Livermore, California.

Growth:

*Habit.*—Bushy; upright; much-branched.

*Growth.*—Vigorous.

*Canes.*—Heavy.

*Main stems.*—Color—Spinach Green, Plate 0960/2. Thorns—many; medium length; hooked downward; with long, narrow base. Prickles—few. Color—Brown, tinged with Bronze. Hairs—none.

*Branches.*—Color—Lettuce Green, Plate 861/1. Thorns—Many; medium length; hooked downward; with long, narrow base. Prickles—few. Color—Brown. Hairs—none.

*New shoots.*—Color—Scheeles Green, Plate 860/2, strongly tinged with Purple Red toward base mainly on side exposed to sun. Thorns—Very many; medium length; hooked downward; with long, narrow base. Prickles—few. Color—Reddish Purple. Hairs—none.

I claim:

A new and distinct variety of rose plant of the hybrid tea class, substantially as herein shown and described, characterized particularly as to novelty by the general similarity of its foliage to that of "Grand Duchess Charlotte" (Plant Patent No. 774), combined with a relatively vigorous, upright and taller habit of growth, longer cutting stems, much longer urn-shaped to long-pointed buds resembling those of the variety "Eclipse" (Plant Patent No. 172), and the velvety, glowing, vivid and unusually uniform Cherry to Orient Red general color tonality of its open flowers.

No references cited.